United States Patent
Pham

(10) Patent No.: US 12,377,041 B2
(45) Date of Patent: *Aug. 5, 2025

(54) COMPOSITIONS CONTAINING PLANT MUCILAGE

(71) Applicant: Peter Pham, Tomball, TX (US)

(72) Inventor: Peter Pham, Tomball, TX (US)

( * ) Notice: Subject to any disclaimer, the term of this patent is extended or adjusted under 35 U.S.C. 154(b) by 735 days.

This patent is subject to a terminal disclaimer.

(21) Appl. No.: 17/444,447

(22) Filed: Aug. 4, 2021

(65) Prior Publication Data

US 2022/0016019 A1  Jan. 20, 2022

Related U.S. Application Data

(63) Continuation-in-part of application No. 16/727,433, filed on Dec. 26, 2019, now Pat. No. 11,110,040, which is a continuation of application No. 16/175,451, filed on Oct. 30, 2018, now Pat. No. 10,517,815, which is a continuation of application No. 15/087,267, filed on Mar. 31, 2016, now Pat. No. 10,117,826.

(51) Int. Cl.

| | | |
|---|---|---|
| *A61K 36/00* | (2006.01) | |
| *A61K 8/02* | (2006.01) | |
| *A61K 8/34* | (2006.01) | |
| *A61K 8/58* | (2006.01) | |
| *A61K 8/9789* | (2017.01) | |
| *A61K 8/9794* | (2017.01) | |
| *A61K 9/70* | (2006.01) | |
| *A61K 36/185* | (2006.01) | |
| *A61K 36/73* | (2006.01) | |
| *A61K 36/752* | (2006.01) | |
| *A61K 36/88* | (2006.01) | |
| *A61K 47/10* | (2017.01) | |
| *A61K 47/24* | (2006.01) | |
| *A61P 29/00* | (2006.01) | |
| *A61Q 19/00* | (2006.01) | |

(52) U.S. Cl.
CPC .......... *A61K 8/9789* (2017.08); *A61K 8/0208* (2013.01); *A61K 8/34* (2013.01); *A61K 8/345* (2013.01); *A61K 8/58* (2013.01); *A61K 8/9794* (2017.08); *A61K 9/70* (2013.01); *A61K 36/185* (2013.01); *A61K 36/73* (2013.01); *A61K 36/752* (2013.01); *A61K 36/88* (2013.01); *A61K 47/10* (2013.01); *A61K 47/24* (2013.01); *A61P 29/00* (2018.01); *A61Q 19/00* (2013.01)

(58) Field of Classification Search
CPC ................................................ A61K 36/752
See application file for complete search history.

(56) References Cited

FOREIGN PATENT DOCUMENTS

CN     105 192 083 A     12/2015

OTHER PUBLICATIONS

Liu, Wenting and Gong, Lan, "Anti-demodectic effects of okra eyelid patch in Demodex blepharitis compared with tea tree oil," Experimental and Therapeutic Medicine 21: 338, 2021, DOI: 10.3892/etm.2021.9769, 8 pages.
Nigo, William OD, et al, "Speed Questionnaire,"1 page, Cornea, "Psychometric Properties and Validation of the Standard Patient Evaluation of Eye Dryness Questionnaire," vol. 32, Issue 9, Sep. 2013, 5 pages.
Schiffman RM, Christianson MD, Jacobsen G, Hirsch JD, Reis BL "Ocular Surface Disease index (OSDI)", 2 pages, https://www.supereyecare.com/resources/OSDI.pdf, Reliability and Validity of the Ocular Surface Disease Index. Archives of Ophthalmology. May 1, 2000;118(5):615-21, 6 pages.
Narayanan, Srihari, et al, "ZEST—Zocular Eyelid System Treatment—improves contact lens discomfort caused by MGD," Optometry's Meeting, 2020, E-poster.
Schachter, Scott, ARVO 6741—B0265 (YR 2019), https://eyedropsdatabase.co.uk/images.documents/ZEST_ARVO_Study_2019.pdf, 1 page.
Extended European Search Report including the Supplementary European Search Report dated Dec. 2, 2019, Appl. No. 17776622.7, 14 pages.
European Search Opinion dated Nov. 15, 2019, Appl. No. EP 177766227, 2 pages.
European Communication dated Oct. 9, 2020, Appl. No. 17776622.7, 4 pages.

*Primary Examiner* — Qiuwen Mi
(74) *Attorney, Agent, or Firm* — Hogan Lovells US LLP

(57) ABSTRACT

A body lubricating, moisturizing, anti-inflammatory, and anti-pain formulation utilizes a mucilage-containing extract derived from a plant such as okra, *Abelmoschus esculentus* (*Hibiscus esculentus*). The formulation can be provided as a free liquid such as a solution, suspension, foam, gel, cream, ointment, or spray or alternatively impregnated into an absorbent solid article such as a mask, a wipe, swab, a bandage, cloth pad or a gauze. Application of the formulation to a mucosal or external bodily tissue result in the application of a layer of mucilage that lubricates and moisturizes the tissue as well as protects it from external damage from foreign particles and UV irradiation. Application of the formulation to an inflamed tissue provides anti-inflammatory effects and relieves pain.

21 Claims, 10 Drawing Sheets

COMPOSITIONS CONTAINING PLANT MUCILAGE

CROSS-REFERENCE TO RELATED APPLICATIONS

This application is a continuation-in-part application of U.S. patent application Ser. No. 16/727,433, filed Dec. 26, 2019; which is a continuation of U.S. patent application Ser. No. 16/175,451, filed Oct. 30, 2018, which issued as U.S. Pat. No. 10,517,815 on Dec. 31, 2019; which is a continuation of U.S. patent application Ser. No. 15/087,267, filed Mar. 31, 2016, which issue as U.S. Pat. No. 10,117,826 on Nov. 6, 2018; all of which are incorporated herein by reference.

BACKGROUND OF THE INVENTION

Field of the Invention

The present invention relates generally to the fields of bodily lubrication and minimization of inflammation. More specifically, the present disclosure provides a formulation comprising plant mucilage for lubricating and moisturizing bodily surfaces, both external and mucosal, for anti-inflammation, and for pain control.

Description of the Related Art

Lubrication plays vital roles in the healthy maintenance of numerous bodily functions. The specific roles vary by the bodily tissue in question.

Tears act as a lubricant for the eyes. Normal ocular function is depending on a clear and smooth layer of tears to support critical ocular surface functions. Tears coat the corneal and conjunctival epithelium to prevent the cells from drying out like those of the skin epithelium, which is a composed of dead cells. With each blink, the tears reduce surface abrasive effect between the eyelid and the corneal surface. The lack of lubrication on the eyes can lead to symptoms of irritation, scratchiness, dryness, and redness. It can also produce scarring, pain, and permanent vision loss.

Saliva is a viscous fluid that acts as the natural lubricant for the mouth. It coats the teeth to prevent tooth decay. It keeps the mouth moist and hydrates food for chewing. The lack of saliva leads to chronic teeth decay, bad breath, swallowing difficulty, and infections.

Even though skin is composed of a layer of dead epithelial cells, lubrication is still needed to maintain the integrity and pliability of the skin. The loss of skin moisture leads to dry, cracked, and flaky skin that increases the risk for infection, bleeding, and pain.

The outer walls of the vagina are coated with a layer of moisture for surface protection, which functions as a natural lubricant for sexual activity and as a barrier to infection and inflammation. The lack of vaginal lubrication can lead to urinary infections, painful intercourse, bleeding, and pain. Lubrication of the rectum performs similar roles.

Mucilage is a viscous gel-like liquid produced by most plants and certain microorganisms. Mucilage is made up of a combination of polysaccharides and proteins. Plants utilize mucilage in diverse life processes such as water storage and seed germination. Individual species of plants vary in the amount of mucilage produced thereby. Examples of plants containing especially high levels of mucilage include various cacti, kelp, various carnivorous plants, mallows, marshmallows, liquorice root, Psyllium, slippery elm bark, and okra, among others.

Okra is a member of the mallow family commonly known for its edible pods rich in mucilage. The current official taxonomic name for okra is *Abelmoschus esculentus*. The *Abelmoschus* genus comprises fifteen species of the mallow family, which were formerly classified within the *Hibiscus* genus. Under the old classification scheme, okra was known as *Hibiscus esculentus*, and this old name is still in common usage. Older classification names for okra from other classification systems include *Abelmoschus bammia; Abelmoschus longifolius; Abelmoschus officinalis; Abelmoschus praecox; Abelmoschus tuberculatus; Hibiscus hispidissimus; Hibiscus longifolius;* and, *Hibiscus praecox*.

The use of okra mucilage as a lubricant for mechanical purposes is known in the previous art. Related U.S. Pat. No. 5,851,963 (O'Bryant, Organic Lubricant, Dec. 22, 1998) and U.S. Pat. No. 6,124,248 (O'Bryant, et al., Organic Lubricants and Coolants, Sep. 26, 2000) provide biodegradable industrial and machining lubricants and coolants derived from mucilage and mucilage extracts. In one embodiment, the mucilage extract is derived from okra, especially okra pods.

U.S. Pat. No. 9,163,374 (Alcantar, et al., Use of cactus mucilage as a dispersant and absorbent for oil in oil-water mixtures, Oct. 15, 2015) teaches the use of cactus and *Hibiscus esculentus* mucilage to remove oil contaminants from water. This method is especially intended for use in cleaning up oil spills.

The prior art also includes previous biomedical applications of okra extracts.

U.S. Pat. No. 4,014,335 (Arnold; Randall K., Ocular Drug Delivery Device, Mar. 29, 1977) teaches the use of okra gum as one of a number of possible drug carriers in a three-layered laminate ocular drug delivery device taught and claimed therein.

U.S. Pat. No. 4,154,822 (Polimeni et al., Polysaccharide for Enhancement of Cardiac Output, May 15, 1979) utilizes polysaccharide substances, preferably derived by extraction and purification of okra plant materials, to provide selective rheological and hemodynamic effects upon biomedical cardiac administration. This method is specifically intended to enhance cardiac output without substantial increments in circulatory (plasma) volume or concurrent inotropic, chronotropic or vasoactive effects.

U.S. Pat. No. 8,628,816 (Henry et al., Product to reduce glycemic response of carbohydrate based foods, Jan. 14, 2014) teaches a method for reducing the glycemic index of a premixed flour by adding various pulverized plant materials, including okra, to the flour. The specification of the patent indicates that the mucilage in the okra plays an important role in reducing the glycemic index of the resulting flour.

US Patent Application No. 20140303094 (Bastia et al., Composition and Use Thereof in the Treatment of Anal Rhagades, Oct. 9, 2014) teaches a medicament for the treatment of anal rhagades that comprises at least one protein extract and/or at least one beta glucan from *Hibiscus*. The *Hibiscus* in question can be *Hibiscus esculentus*.

The prior art is deficient in the lack of an okra mucilage containing lubricating and moisturizing formulation for external and mucosal body surfaces. The present disclosure addresses this lack.

SUMMARY OF THE INVENTION

An embodiment of the disclosure is a formulation for lubricating, moisturizing, anti-inflammation, and for pain control for application to a bodily tissue (examples include but are not limited to skin, joints, subcutaneous tissue, visceral organs, mucosal membrane, cartilage, gum, tendons) comprising mucilage extracted from one or more plant species, wherein the formulation is intended to be applied to a bodily tissue. In an embodiment, the plant species is from a plant genus selected from the group comprising *Abelmoschus* and *Hibiscus*. In an embodiment, wherein the mucilage is extracted from *Abelmoschus esculentus* (*Hibiscus esculentus*). In an embodiment, the mucilage is extracted from plant material selected from the group comprising fresh plant material, frozen plant material, dried plant material, and powdered plant material. In an embodiment, the formulation is buffered to a pH range of about 5.5 to 8.0. In an embodiment, the formulation is buffered to a pH of about 6.5. In an embodiment, the formulation is buffered with one of more salts selected from the list comprising sodium chloride, sodium lactate, potassium chloride, and calcium chloride. In an embodiment, the formulation further comprises one or more cationic, anionic, nonionic, or amphoteric surfactants. In an embodiment, the one or more surfactants are selected from the group comprising cocamidopropyl betaine disodium laureth sulfosuccinate; cetalkonium chloride; decyl glucoside; disodium cocoamphodiacetate; and glycerin. In an embodiment, the formulation further comprises one or more emollients. In an embodiment, the one or more emollients are selected from the group comprising *Aloe barbadensis* leaf juice; and glycerin. In an embodiment, the formulation further comprises one or more antioxidants. In an embodiment, the one or more antioxidants are selected from the list comprising *Rubus idaeus* (Raspberry) seed oil and *Citrus unshiu* peel extract. In an embodiment, the formulation further comprises caffeine as an antioxidant; sodium phytate as a chelating agent; hydrolyzed soy protein as a moisturizer; ethylhexylglycerin as a conditioning agent and preservative; and phenoxyethanol as a preservative. In an embodiment, the formulation is provided in a form selected from the group comprising a wipe; a swab; a bandage; a gauze; a suspension; a foam; and a spray.

An embodiment of the disclosure is a lubricating, moisturizing, anti-inflammatory, and anti-pain formulation comprising *Abelmoschus esculentus* (*Hibiscus esculentus*) (okra) mucilage; *Rubus idaeus* (raspberry) seed oil; *Citrus unshiu* peel extract; *Aloe barbadensis* leaf juice; sodium phytate; phenoxyethanol; ethylhexylglycerin; wherein the formulation is buffered to a pH range of about 5.5 to 8.0. In an embodiment, the *Abelmoschus esculentus* (*Hibiscus esculentus*) mucilage has been extracted from plant material selected from the group comprising fresh plant material, frozen plant material, dried plant material, and powdered plant material. In an embodiment, the *Abelmoschus esculentus* (*Hibiscus esculentus*) mucilage is extracted from powdered okra.

In an embodiment, the formulation is provided in a form selected from the group comprising a wipe; a swab; a bandage; a gauze; a suspension; a foam; and a spray.

An embodiment of the disclosure is an eyelid cleansing and moisturizing wipe, the wipe comprising a cloth pad impregnated with a formulation comprising *Abelmoschus esculentus* (*Hibiscus esculentus*) (okra) mucilage; *Rubus idaeus* (raspberry) seed oil; *Citrus unshiu* peel extract; *Aloe barbadensis* leaf juice; disodium laureth sulfosuccinate; cetalkonium chloride; decyl glucoside; disodium cocoamphodiacetate; glycerin; caffeine; sodium phytate; hydrolyzed soy protein; phenoxyethanol; ethylhexylglycerin; sodium chloride; sodium lactate; potassium chloride; and calcium chloride; wherein the formulation is buffered to about pH 6.5.

A body lubricating, moisturizing, and anti-inflammatory formulation comprising plant mucilage is provided by the disclosure described and claimed herein. More specific embodiments of the described formulation utilize plant mucilage extracted from a species of either the *Abelmoschus* or *Hibiscus* genus, especially mucilage from okra (*Abelmoschus esculentus*, still commonly described by its older scientific classification name *Hibiscus esculentus*).

A number of other components can be included in the formulation to improve its properties and function. *Rubus idaeus* (raspberry) seed oil and *Citrus unshiu* peel extract can be added to provide antioxidant properties. Surfactant activity can be incorporated into the formulation by introducing disodium laureth sulfosuccinate, cetalkonium chloride; decyl glucoside, disodium cocoamphodiacetate and/or glycerin. Glycerin can also be added as an emollient in the formulation. *Aloe barbadensis* leaf juice can also be used as an additional emollient. Caffeine is a useful addition for its antioxidation properties. Sodium phytate can be added as a chelating agent. Moisturizers such as hydrolyzed soy protein and ethylhexylglycerin can play useful roles in the formulation. Ethylhexylglycerin also has preservative qualities and can be included along with phenoxyethanol for this purpose.

This formulation can be proved as a free liquid solution, suspension, foam, gel, cream, ointment, or spray. Alternatively, the formulation can be impregnated onto a wipe, a swab, a bandage, or gauze. An eye wipe comprising a cloth pad wetted with the above formulation is specifically provided and claimed herein.

BRIEF DESCRIPTION OF THE DRAWINGS

So that the matter in which the above-recited features, advantages and objects of the disclosure, as well as others which will become clear, are attained and can be understood in detail, more particular descriptions of the disclosure briefly summarized above can be had by reference to certain embodiments thereof which are illustrated in the appended drawings. These drawings form a part of the specification. It is to be noted, however, that the appended drawings illustrate preferred embodiments of the disclosure and therefore are not to be considered limiting in their scope.

FIG. 1 shows a biological tissue both before and after the application of the lubricating and moisturizing mucilage formation provided herein. Prior to the application of the mucilage formulation, the tissue is more susceptible to damage by foreign particles and UV rays as well as water loss through evaporation. Application of the mucilage containing lubricating and moisturizing formulation provides a protective barrier against both foreign particles and UV rays as well as aiding in water retention.

FIGS. 3A-3C depict cylindrical dandruff present at the eyelash roots (arrows).

FIG. 3D does not depict cylindrical dandruff present at the eyelash roots.

DETAILED DESCRIPTION OF THE INVENTION

Figure 1:
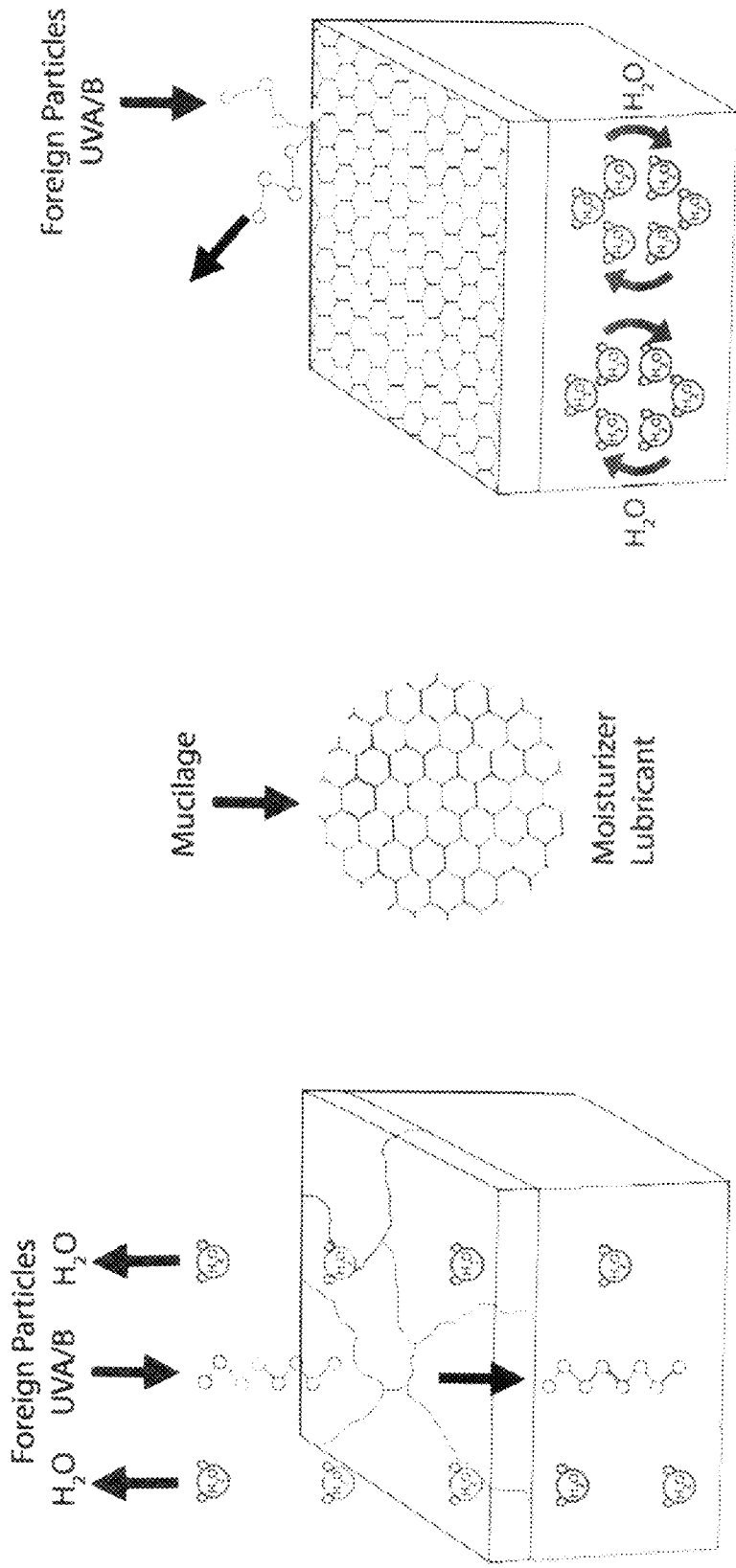
FIG. 1 illustrates the protective qualities of the lubricating and moisturizing formulation of the instant disclosure.

Therefore, if appearing herein, the following terms shall have the definitions set out below.

Lubricate, as used herein, refers to the addition of anything which reduces friction.

Moisturize, as used herein, describes an action that increases water content or aids in water retention in a biological tissue.

Inflammation, as used herein, is a pathologic response that can be provoked by physical, chemical, and biologic agents. The response can include but is not limited to cytologic changes, cellular infiltration, and/or mediator release. Pain is the subjective sensation of discomfort that can vary from mild to unbearable. The neural sensors for pain, called nociceptors, can be classified according to the type of stimulus that triggers them. Hence there are chemical nociceptors, thermal nociceptor, mechanical nociceptors, and some nociceptors respond to multiple types of painful stimuli. The final pathway for all clinically relevant pain is inflammatory pain, which occurs when there has been damage to tissue from mechanical, thermal, or chemical injury or when there is an autoimmune type injury where the inflammation is due to an intrinsic rather than an extrinsic process. As an example, pinching on the skin activates the mechanical nociceptors but the pain from the pinch will quickly dissipates once the force of the pinch has been removed. However, if the force of the pinch is strong enough to cause tissue damage, there will be secondary inflammatory pain that will not quickly improve even if the mechanical nociceptors are no longer activated.

Mucilage, as used herein, is a polysaccharide substance extracted as a viscous or gelatinous solution from plants and microorganisms. Mucilage can also contain proteins and plays a variety of roles in plant life functions. Isolated mucilage can be used as a lubricant.

As used herein, a surfactant is a chemical compound, usually organic, used to reduce the surface tension between two liquids or between a liquid and a solid. Various detergents, wetting agents, emulsifiers, foaming agents, and dispersants are among the agents that can be used as surfactants.

As described herein. a moisturizer is a chemical substance or combination thereof which hydrates biological tissues, usually by preventing water evaporation from the tissues.

An emollient, as used herein, is a compound or mixture of compounds that are used to moisturize skin to reduce water loss and provide a protective cover. Applications of emollients to skin have a soothing and smoothening effect on the skin, making the skin softer and more pliable.

A conditioning agent, as used herein, refers to any compound or combination thereof, provide a soft improved feel and texture to a biological tissue. Conditioning agents are added to various creams and lotions, gels, serums, facial spray mists, skin toners, shampoos, hair styling gels, hair sprays and hair conditioners.

As used herein, antioxidants are molecules that prevent oxidation. By preventing oxidation, antioxidants protect biological tissues from both the oxidation process itself and from the free radicals that can be produced during the same process. The production of free radicals can result in chain reactions that can result in considerable damage to biological tissues. Various thiols such as glutathione and ascorbic acid (vitamin C) are examples of antioxidants.

A vasoconstrictor, as used herein, is a chemical agent that narrows blood vessels by contracting the muscular wall of the vessels. This results in reduce blood flow to the affected area. This has a cooling effect on the affected tissue.

A chelating agent is an organic molecule which can bind a metal or metal ion. Chelating agents are useful for removing metal and metal ions from an environment by binding and thus sequestering them.

A buffer, as used herein, refers to anything that stabilizes the pH of a solution. Various chemicals and salt combinations are effective buffers.

A preservative, as used herein, refers to a chemical that is added to products such as food, beverages, pharmaceutical drugs, paints, biological samples, cosmetics, wood, and many other products to prevent either chemical or microbial degradation of the product in question.

In an embodiment, the formulation can be used to treat mammals. In an embodiment, the formulation can be used to treat humans.

Figure 2:
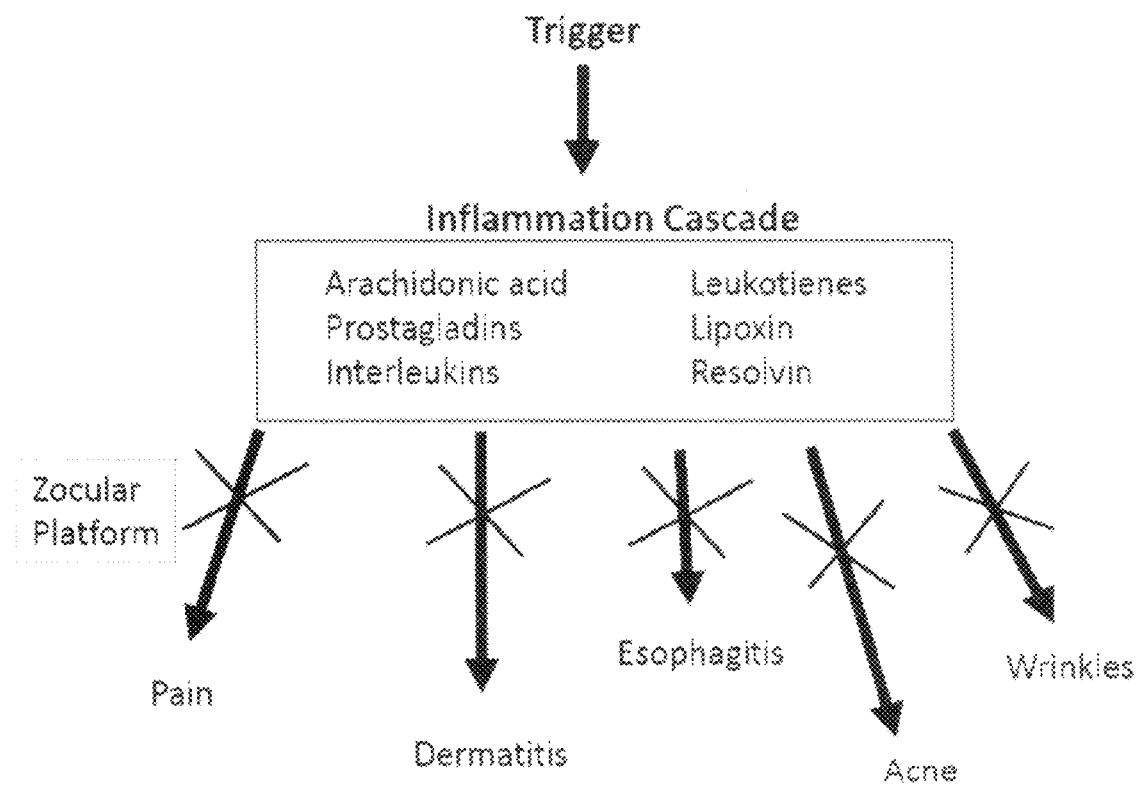
FIG. 2 illustrates various inflammation pathways and the effect of the mucilage-based platform described herein.
Figures 3A, 3B, 3C, 3D:
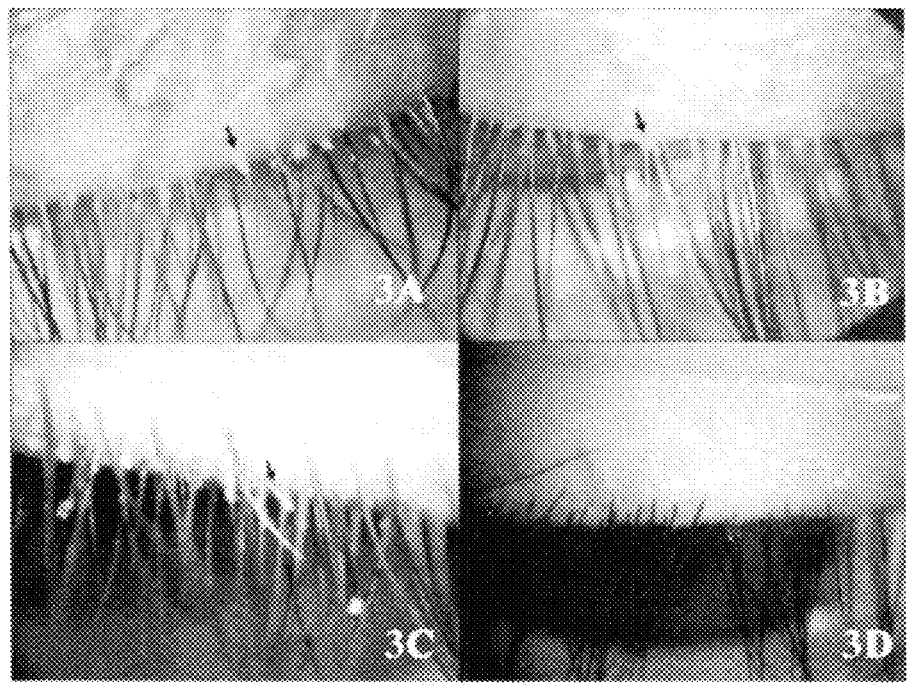
FIG. 3A-3D depict photographs of the eyelid and eyelashes of patients with blepharitis.

The body formulation described and claimed herein has anti-inflammatory properties for biological tissues. Inflammation is characterized by the release of inflammatory mediators such cytokines, prostaglandins, and histamines. The three major components of the inflammatory process are 1) hemodynamic changes; 2) increased capillary permeability; and 3) leukocytic exudation. The signs of inflammation include some or all of 1) heat; 2) redness; 3) swelling; 4) pain; and 5) loss of function or structural integrity. In an embodiment, the inflammation can be aphthous ulcer, arteritis, arthritis, balanitis, blepharitis, bronchitis, bursitis, cellulitis, cheilitis, cholecystitis, colitis, conjunctivitis, dermatitis, encephalitis, endocarditits, enteritis, episcleritis, esophagitis, funiculitis, gastritis, gingivitis, glossitis, hepatitis, keratitis, laryngitis, lymphadenitis, meibomianitis meningitis, metritis, myelitis, myocarditis, myositis, nephritis, odontitis, omphaloitis, oophoritis, ophthalmitis, orchitis, osteitis, osteomyelitis, otitis, pericarditis, splenitis, tracheitis, periostitis, and vaginitis. In an embodiment, the inflammation can be other than at a location mentioned above. In an embodiment, the inflammation can be secondary to a primary infection, cancer, or photodamage from lasers, x-rays, gamma rays, or sun exposure. In an embodiment, the composition can be used to treat dry eyes, dry socket, acne, pain, wrinkles, fine lines on skins, or numb tissue. FIG. 2 illustrates various inflammation pathways and the effect of the mucilage-based platform described herein.

In an embodiment, the % range can refer to about the lower percentage to about the higher percentage.

The formulation is able to reduce acute pain within minutes (or seconds on mucosal tissue). Applying the formulation to an inflamed joint will result in a 60-90% reduction in pain within 15-20 minutes that will last for hours, with the duration of relief increasing over time. The formulation is able to be absorbed through the skin.

The body formulation described and claimed herein is capable of lubricating and moisturizing both mucosal and external biological tissues (FIG. 1) and acting as an anti-inflammatory (FIG. 2). The formulation in question utilizes mucilage extracted from plant materials from one or more plant species to achieve this end. The formulation in question can also be used an anti-inflammatory or anti-pain agent over a small area or in low or minute dosage where its lubricating or moisturizing effects would not be as significant as its anti-pain or anti-inflammation effects. The mucilage can be extracted from a number of different types of plant materials including fresh plant material, frozen plant material, dried plant material, and powdered plant material. The concentration of plant mucilage in the formulation can range from 0.001 to 5.0%.

In more specific embodiments of the instant disclosure, the mucilage containing extract is derived from one or more plant species of either the *Abelmoschus* genus or the *Hibiscus* genus of plant species. In a preferred embodiment of the instant disclosure, the mucilage is derived from the okra plant, also known by its current scientific name *Abelmoschus esculentus* and formerly known as *Hibiscus esculentus*.

The body lubricating and moisturizing formulation can be buffered to a pH range of about 5.5 to 8.0. Buffering the formulation to about pH 6.5 is an embodiment of the instant disclosure. This can be accomplished with a combination of salts including but not limited to sodium chloride, sodium lactate, potassium chloride, and calcium chloride. The relative amount of each salt is balanced to achieve the desired pH. The concentrations of the individual salts can range from 0.001-2.0% in the instant disclosure.

The formulation of the instant disclosure can also include surfactants. Possible surfactants and possible concentration thereof include: disodium laureth sulfosuccinate (0.01-12%); cetalkonium chloride (0.01-40%); decyl glucoside (0.01-12.0%), disodium cocoamphodiacetate (0.01-4.0%); and glycerin (0.008-0.5%). The formulation can also include one or more emollients, which can include *Aloe barbadensis* leaf juice (0.05-4.0%). and glycerin (0.008-0.5%).

One or more antioxidants can be included in the formulation of the instant disclosure to prevent oxidative damage to the tissues to which it is applied. *Rubus idaeus* (Raspberry) seed oil (0.03-1.0%) and *Citrus unshiu* peel extract (0.01%-1.0%) are preferred antioxidants.

A number of additional components can be incorporated in the lubricating and moisturizing formulation. Caffeine, at concentration range 0.05-0.5%, can be added as an antioxidant. Sodium phytate (concentration range of 0.02-1.0%) can be included as a chelating agent. Including hydrolyzed soy protein at 0.025-3.0% concentration increases the ability of the formulation to moisturize bodily tissues. 0.001-1.0% ethylhexylglycerin is a useful addition as a preservative carrier agent. The preservative phenoxyethanol can also be used at a concentration range of 0.01-1.0%. In an embodiment, the composition is comprised of the contents of Table 1.

TABLE 1

| Substance | Range (%) (w/v) |
|---|---|
| Plant mucilage | 0.001-5.0 |
| Emollients (at least one): | |
| *aloe barbadensis* leaf juice | 0.05-4.0 |
| glycerin | 0.008-0.5 |
| Antioxidants (at least one): | |
| *Rubus idaeus* seed oil | 0.03-1.0 |
| *Citrus unshiu* peel extract | 0.01-1.0 |
| Chelating agent (optional): | |
| sodium phytate | 0.02-1.0 |
| Preservative carrier agent (optional) | |
| ethylhexylglycerin | 0.001-1.0 |
| phenoxyethanol | 0.01-1.0 |
| Water | 60-95 |

In an embodiment, the composition is comprised of the contents of Table 2.

TABLE 2

| Substance | Range (%) (w/v) |
|---|---|
| Plant mucilage | 0.001-5.0 |
| Salts (at least one): | |
| sodium chloride | 0.001-2.0 |
| sodium lactate | 0.001-2.0 |
| potassium chloride | 0.001-2.0 |
| calcium chloride | 0.001-2.0 |
| Surfactants (at least one): | |
| disodium laureth sulfosuccinate | 1.0-12.0 |
| decyl glucoside | 1.0-12.0 |
| disodium cocoamphodiacetate | 0.1-4.0 |
| glycerin | 0.008-0.5 |
| cetalkonium chloride | 0.01-40 |
| Emollients (at least one): | |
| *aloe barbadensis* leaf juice | 0.05-4.0 |
| glycerin | 0.008-0.5 |
| Antioxidants (at least one): | |
| *Rubus idaeus* seed oil | 0.03-1.0 |
| *Citrus unshiu* peel extract | 0.01-1.0 |
| Caffeine (optional) | 0.05-0.5 |
| Chelating agent (optional): | |
| sodium phytate | 0.02-1.0 |
| Hydrolyzed soy protein (optional) | 0.025-3.0 |
| Preservative carrier agent (optional) | |
| ethylhexylglycerin | 0.001-1.0 |
| Preservative (optional): | |
| phenoxyethanol | 0.01-1.0 |
| Fragrance | 0-0.25 |
| Water | 60-95 |

In an embodiment, the composition does not contain at least one ingredient from each row shown in Table 1. In an embodiment, the composition contains at least plant mucilage. In an embodiment, the composition does not include surfactants or emulsifiers. In an embodiment, the composition contains plant mucilage, at least one emollient, at least one antioxidant, a chelating agent, and water. In an embodiment, the composition contains plant mucilage, at least one emollient, at least one antioxidant, a chelating agent, water, and at least one preservative carrier agent. In an embodiment, the composition does not include at least one salt, at least one surfactant, caffeine, and at least one preservative carrier agent and fragrance. In an embodiment, the composition includes no preservative. In an embodiment, a sterile production process and/or packaging is used. In an embodiment, the composition does not include water. In an embodiment, the composition includes oil or a non-aqueous carrier.

The body lubricating, moisturizing, anti-inflammatory formulation of the claimed herein can be provided in a number of possible forms. Free liquid or fluid forms include solutions, parenteral, intravenous, intrathecal, gels, creams, ointments, suspensions, foams, and sprays. Alternatively, the formulation can be impregnated onto a physical object such as a wipe; a swab; a bandage; a transdermal patch; or a gauze.

In an embodiment, the effect of the formulation lasts at least 10-60 minutes. In an embodiment, the effect of the formulation lasts at least 1-24 hours.

A preferred embodiment of the instant disclosure is a body lubricating and moisturizing formulation comprising a combination of *Abelmoschus esculentus* (*Hibiscus esculentus*) (okra) mucilage; *Rubus idaeus* (raspberry) seed oil; *Citrus unshiu* peel extract; *Aloe barbadensis* leaf juice; cocamidopropyl betaine; disodium laureth sulfosuccinate; cetalkonium chloride; decyl glucoside; disodium cocoamphodiacetate; glycerin; caffeine; sodium phytate; hydrolyzed soy protein; phenoxyethanol; ethylhexylglycerin; sodium chloride; sodium lactate; potassium chloride; and, calcium chloride. The above combination can be buffered to a pH range of 5.5 to 8.0, with 6.5 being a preferred pH. The *Abelmoschus esculentus* mucilage can be derived from at least one of fresh plant material, frozen plant material, dried plant material, and powdered plant material. The particular embodiment described in the examples provided herein utilizes powdered okra. This solution can be provided as a free suspension or solution, possibly as a foam or spray. In an embodiment, the liquid can be applied using a dropper. Alternatively, the formulation can be provided as liquid absorbed onto a mask, a wipe, a swab, a bandage, or gauze.

Another preferred embodiment of the instant disclosure is an eyelid cleansing and moisturizing eye wipe wetted with the formulation described and claimed herein. Specifically, this formulation is a mixture of *Abelmoschus esculentus* (*Hibiscus esculentus*) (okra) mucilage; *Rubus idaeus* (raspberry) seed oil; *Citrus unshiu* peel extract; *Aloe barbadensis* leaf juice; disodium laureth sulfosuccinate; cetalkonium chloride; decyl glucoside; disodium cocoamphodiacetate; glycerin; caffeine; sodium phytate; hydrolyzed soy protein; phenoxyethanol; ethylhexylglycerin; sodium chloride; sodium lactate; potassium chloride; and, calcium chloride; wherein the formulation is buffered to a pH range of about 5.5 to 8.0. In an embodiment, the pH is about 6.5.

The following examples are embodiments of the disclosure and are not meant to limit the present disclosure in any fashion.

EXAMPLE 1

Preparation of Mucilage

The mucilage can be prepared by any method or purchased from a commercial source.

EXAMPLE 2

Body Lubricating Composition

A sample prototype composition of the instant disclosure was formulated as an aqueous solutions containing a mixture of mucilage extracted from okra (*Abelmoschus esculentus* or *Hibiscus esculentus*) powder; *Rubus idaeus* (raspberry) seed oil; *Citrus unshiu* peel extract; *Aloe barbadensis* leaf juice; cocamidopropyl betaine; disodium laureth sulfosuccinate; decyl glucoside; disodium cocoamphodiacetate; glycerin; caffeine; Sodium Phytate; hydrolyzed soy protein; phenoxyethanol; ethylhexylglycerin; sodium chloride; sodium lactate; potassium chloride; and calcium chloride.

The okra mucilage provides the main lubricating and moisturizing quality of the formulation. The acceptable concentration range for the okra powder mucilage is of 0.001-5.0% (w/v). In addition to powdered okra, it would be possible to extract the mucilage in the formulated composition from fresh, frozen, or dried okra.

The formulation was preferentially buffered to a pH range of about 5.5 to 8.0, with a preferable pH of about 6.5. The buffering was accomplished with a combination of sodium chloride; sodium lactate; potassium chloride; and calcium chloride. The concentration ranges of each salt used to attain the desired pH in question were as follows: sodium chloride: 0.3-2.0%; sodium lactate: 0.2-2.0%; potassium chloride: 0.01-2.0%; and calcium chloride: 0.01-2.0%.

In an embodiment, the following agents were incorporated as surfactants in the formulations at the given concentration ranges: cocamidopropyl betaine (1.0-12%); disodium laureth sulfosuccinate (1.0-12%); decyl glucoside (1.0-12.0%); disodium cocoamphodiacetate (0.1-4.0%); and glycerin (0.008-0.5%). The glycerin provides a dual role in the formation in that it also acts as an emollient. *Aloe barbadensis* leaf juice was also added as another emollient at a concentration range of 0.05-4.0%.

In an embodiment, *Rubus idaeus* (Raspberry) seed oil and *Citrus unshiu* peel extract were included for their antioxidant properties. The raspberry seed oil was added in concentration range of 0.001-5.0%, while the *Citrus unshiu* peel extract was present at concentrations of 0.01%-1.0%.

In an embodiment, caffeine, at concentration range of 0.05-0.5%, was used as an antioxidant. In an embodiment, sodium phytate, a chelating agent, and was added at a concentration range of 0.02-1.0%. In an embodiment, hydrolyzed soy protein at a concentration range of 0.025-3.0% was added as an additional moisturizer.

In an embodiment, ethylhexylglycerin was included as both a moisturizer and a preservative at a concentration range of 0.001-1.0%. In an embodiment, the phenoxyethanol was also used as a preservative at concentrations of 0.01-1.0%. In an embodiment, fragrance can be added at concentrations up to 0.25%.

Following the addition of the above components, the remaining aqueous portion of the above described formulation can range from 60-95%.

EXAMPLE 3

Anti-Inflammatory and Anti-Pain Composition

A sample prototype composition of the instant disclosure was formulated as an aqueous solutions containing a mixture of mucilage extracted from okra (*Abelmoschus esculentus* or *Hibiscus esculentus*) powder; *Rubus idaeus* (raspberry) seed oil; *Citrus unshiu* peel extract; *Aloe barbadensis* leaf juice; cocamidopropyl betaine; disodium laureth sulfosuccinate; decyl glucoside; disodium cocoamphodiacetate; glycerin; caffeine; Sodium Phytate; hydrolyzed soy protein; phenoxyethanol; ethylhexylglycerin; sodium chloride; sodium lactate; potassium chloride; and calcium chloride.

The okra mucilage provides the main lubricating and moisturizing quality of the formulation. The acceptable concentration range for the okra power mucilage is of 0.001-5.0% (w/v). In addition to powered okra, it would be possible to extract the mucilage in the formulated composition from fresh, frozen, or dried okra. The extract can be made from the seed, root, capsule, leaves, or any combination thereof.

The formulation was preferentially buffered to a pH range of 5.5 to 8.0, with a preferable pH of about 6.5. The buffering was accomplished with a combination of sodium chloride; sodium lactate; potassium chloride; and, calcium chloride. The concentration ranges of each salt used to attain the desired pH in question were as follows: sodium chloride: 0.3-2.0%; sodium lactate: 0.2-2.0%; potassium chloride: 0.01-2.0%; and calcium chloride: 0.01-2.0%.

The following agents were incorporated as surfactants in the formulations at the given concentration ranges: cocamidopropyl betaine (1.0-12%); disodium laureth sulfosuccinate (1.0-12%); decyl glucoside (1.0-12.0%); disodium cocoamphodiacetate (0.1-4.0%); and, glycerin (0.008-0.5%). The glycerin provides a dual role in the formation in that it also acts as an emollient. *Aloe barbadensis* leaf juice was also added as another emollient at a concentration range of 0.05-4.0%.

*Rubus idaeus* (Raspberry) seed oil; and, *Citrus unshiu* peel extract were included for their antioxidant properties. The raspberry seed oil was added in concentration range of 0.001-5.0%, while the *Citrus unshiu* peel extract was present at concentrations of 0.01%-1.0%.

Caffeine, at concentration range of 0.05-0.5% was used an antioxidant. Sodium Phytate, a chelating agent, and was added at concentration range of 0.02-1.0%. Hydrolyzed soy protein at concentration range of 0.025-3.0% was added as an additional moisturizer.

Ethylhexylglycerin was included as both a moisturizer and a preservative at a concentration range of 0.001-1.0%. The phenoxyethanol was also used as a preservative at concentrations of 0.01-1.0%. Fragrance can be added at concentrations up to 0.25%.

Following the addition of the above components, the remaining aqueous portion of the above described formulation can range 60-95%.

EXAMPLE 4

Wipes

For convenience, cotton pads were impregnated with the above aqueous. The pads provide a more convenient method of applying the formulation. These pads are especially useful as eye wipes. In an embodiment, the pads can be comprised of including but not limited to cotton, paper, tissue, fiber, non-woven fabric, plastic, or polyester.

EXAMPLE 5

Application of the Formulation to a Biological Tissue.

The lubricating and moisturizing formulation provided herein acts as a lubricating, moisturizing and protective barrier to the tissues to which it is applied. These effects are illustrated in FIG. 1. The unprotected tissue shown on the left is susceptible to both water loss and assault from foreign particles and UV rays. The application of the lubricating and moisturizing formulations of the instant disclosure result in a protective layer of mucilage being applied to the surface of the tissue to which it applies. This layer provides a barrier against UV rays and foreign particles. In addition, the resulting barrier prevents water loss from the tissue in question, thereby acting as a moisturizer.

EXAMPLE 6

Results of Using the Formulation

The formulation has been shown in a clinical in vitro study to kill ocular *Demodex* mites. The aim of the study was to determine the efficacy of ZocuFoam™ Eyelid Cleanser & Moisturizer at killing *Demodex* mites. The control was preservative-free saline and the topical agent was ZocuFoam™ Eyelid Cleanser & Moisturizer. Patients who exhibited cylindrical sleeves on their lashes were selected and a slit lamp exam was performed to determine which lashes would be epilated. The lashes were then immersed in an agent and examined with a light microscope. The presence of *Demodex* was determined and the amount of time for the agent to completely kill the *Demodex* mite was noted. Kill time was determined by the cessation of leg movements of the mites for a period of 10 minutes. On average, ZocuFoam™ and preservative-free saline killed *Demodex* in 91.11±38.15 and 1129.78±158.38 minutes (p=0.001), respectively. ZocuFoam™ effectively killed *Demodex* significantly faster than preservative-free saline. In an embodiment, the ingredients of ZocuFoam™ are water, cocamidopropyl betaine, disodium laureth sulfosuccinate, decyl gluoside, disodium cocoamphodiacetate, *Aloe barbadensis* leaf juice, *Rubus idaeus* seed oil, *Citrus unshiu* peel extract, *Hibiscus esculentus* powder, caffeine, sodium phytate, hydrolyzed soy protein, glycerin, ethylhexylglycerin, phenoxyethanol, fragrance.

Blepharitis is an inflammation of the eyelids that causes redness, irritation, an itchy sensation, and the formation of dandruff-like scales on eyelashes. It involves inflammation of the eyelid margin where the eyelashes are attached and causes irritation, redness, and tissue damage. Many causes of blepharitis, both anterior and posterior, have been described; however the current study is particularly concerned with ocular *Demodex* infestation.

Of the many species of *Demodex* mites known to exist, *Demodex folliculorum* and *Demodex brevis* are the only two found living on the human body. *D. folliculorum* is primarily found in hair follicles, while *D. brevis* is found associated with sebaceous and meibomian glands connected to hair follicles (Gao et al., Brit. J. of Ophthal. (2005)). Both species generally inhabit areas on the face, near the nose, eyelashes, and eyebrows, but they can also occur elsewhere on the body.

Patients with blepharitis often present with cylindrical dandruff on their eyelashes. FIG. 3A-3D. Cylindrical dandruff (CD) are scales that form clear cuff collars around eyelash roots (Gao et al., Invest. Ophthal. & Visual Sci. (2005)). This is often indicative of the presence of ocular *Demodex* because it is regarded as pathognomonic of *Demodex* infestation (Gao et al., Invest. Ophthal. & Visual Sci. (2005)). An okra eyelid patch has been shown to have anti-demodectic effects (Liu and Gong, Experimental and Therapeutic Medicine (2021)).

Materials included 0.9% preservative-free saline (Hospira, Inc., Lakeforest, IL) and ZocuFoam™ Eyelid Cleanser & Moisturizer (Okra Limited, Cypress, TX) (water, cocamidopropyl betaine, disodium laureth sulfosuccinate, decyl gluoside, disodium cocoamphodiacetate, *Aloe barbadensis* leaf juice, *Rubus idaeus* seed oil, *Citrus unshiu* peel extract, *Hibiscus esculentus* powder, caffeine, sodium phytate, hydrolyzed soy protein, glycerin, ethylhexylglycerin, phenoxyethanol, fragrance).

The study was conducted at the Cross Eye Centers according to the tenets espoused in the Declaration of Helsinki. A total of 9 patients were selected, who displayed evidence of anterior blepharitis. A slit lamp was used to examine the patient population to determine that those selected evinced cylindrical dandruff around at least 8 eyelashes. Based on previous studies, cylindrical dandruff on 8 eyelashes is sufficient to indicate a modest infestation of ocular *Demodex*. The patient selection was not exclusive based on age, ethnicity, or gender. The only patients excluded from the study were those who were currently on a tea tree oil treatment regimen or those who had undergone fluorescein staining. This exclusion was made because the *Demodex* derived from these patients might exhibit a shortened survival time due to prior exposure to these agents.

One affected eyelash from each fourth of the upper eyelids was epilated using a jeweler's type forceps and a slit lamp microscope (Haag-Streit, Bern, Switzerland). Using this method, 43 lashes were collected—18 of which exhibited *Demodex*.

Each individual eyelash was placed on a microscope slide and immediately saturated with 20 µL of either ZocuFoam™ or preservative-free saline. A plastic coverslip was then placed over the mixture and the slide was examined. Under the microscope, the presence of living adult *Demodex* was examined. Confirmation of the mites' live status was evidenced by vigorous movement of their four pairs of legs. Adult *Demodex* is distinguishable from juvenile *Demodex* because of its well-formed legs, stumpy body, and length of approximately 0.4 mm (Gao et al., Invest. Ophthal. & Visual Sci. (2005)).

Once the determination was made that mites were present and alive on the slides, the mites were observed every 15 to 30 minutes to check for obvious signs of reduction of leg movement. When it became apparent that only one of its legs was moving irregularly, the mite under observation was watched continuously until its leg ceased to move.

The mites were observed for a period of 10 additional minutes following the cessation of leg movement in order to establish the accuracy of the recorded kill time. Kill time is calculated as the time between exposure of the mite to the agent and cessation of mite leg movement for a period longer than 10 minutes.

Figure 4:
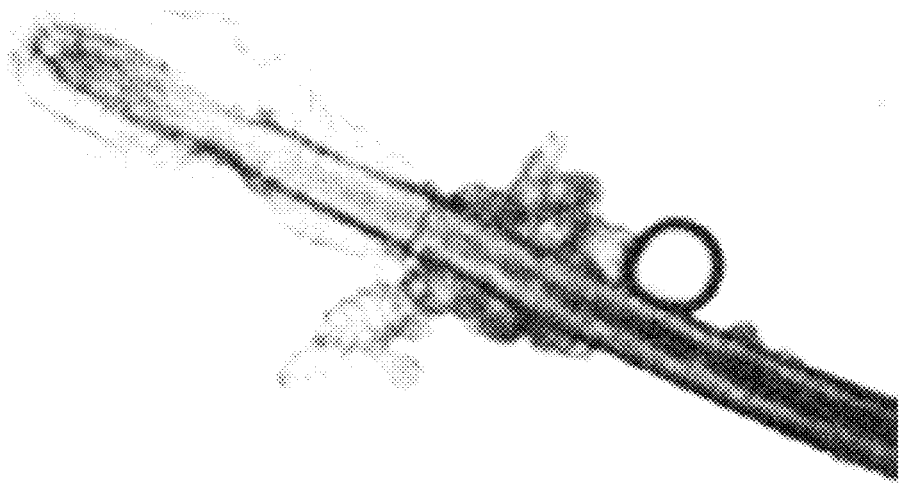
FIG. 4 depicts a view of *Demodex folliculorum* adult and egg forms located on an eyelash follicle. Inceboz et al. (2009).

*Demodex* were excluded from the study if they did not have vigorous leg movements at the beginning of observation or if more than half of their bodies were encased in cylindrical dandruff. FIG. 4 depicts a view of *Demodex folliculorum* adult and egg forms located on an eyelash follicle.

TABLE 3

Resultant mean kill time of the test agents

|  | ZocuFoam ™ (mean ± SD) | Preservative-free Saline (mean ± SD) |
|---|---|---|
| Mean kill time (minutes) | 91.11 ± 38.15 | 1129.778 ± 158.38 |
| N = number of *Demodex* mites | 9 | 9 |

Results from a t-test used to analyze the data shows a significant difference in kill time of the *Demodex* between ZocuFoam™ and preservative-free saline (p<0.0001). Table 3.

In this in vitro study of the effects of applying topical and eyelid cleansing agents to *Demodex* derived from patients with anterior blepharitis, ZocuFoam™ is effective in eradicating the mites in a timely manner when compared to saline. ZocuFoam™ was able to kill the *Demodex* on average in 1.52 hours. The preservative-free saline was able to kill the *Demodex* on average in 18.83 hours.

According to Gao (Gao et al., Brit. J. of Ophthal. (2005)), Tea Tree Oil (TTO) stimulates *Demodex* to migrate out of cylindrical dandruff casings embedded in the skin, allowing them to encounter the oil. Although it is understood that TTO is a very effective cleansing agent, its use among patient populations may not be as high as expected because TTO acts as an irritant if it enters a patient's eyes. This issue may be circumvented if patients are warned beforehand to tightly seal their eyelids before applying the oil.

Figure 5:
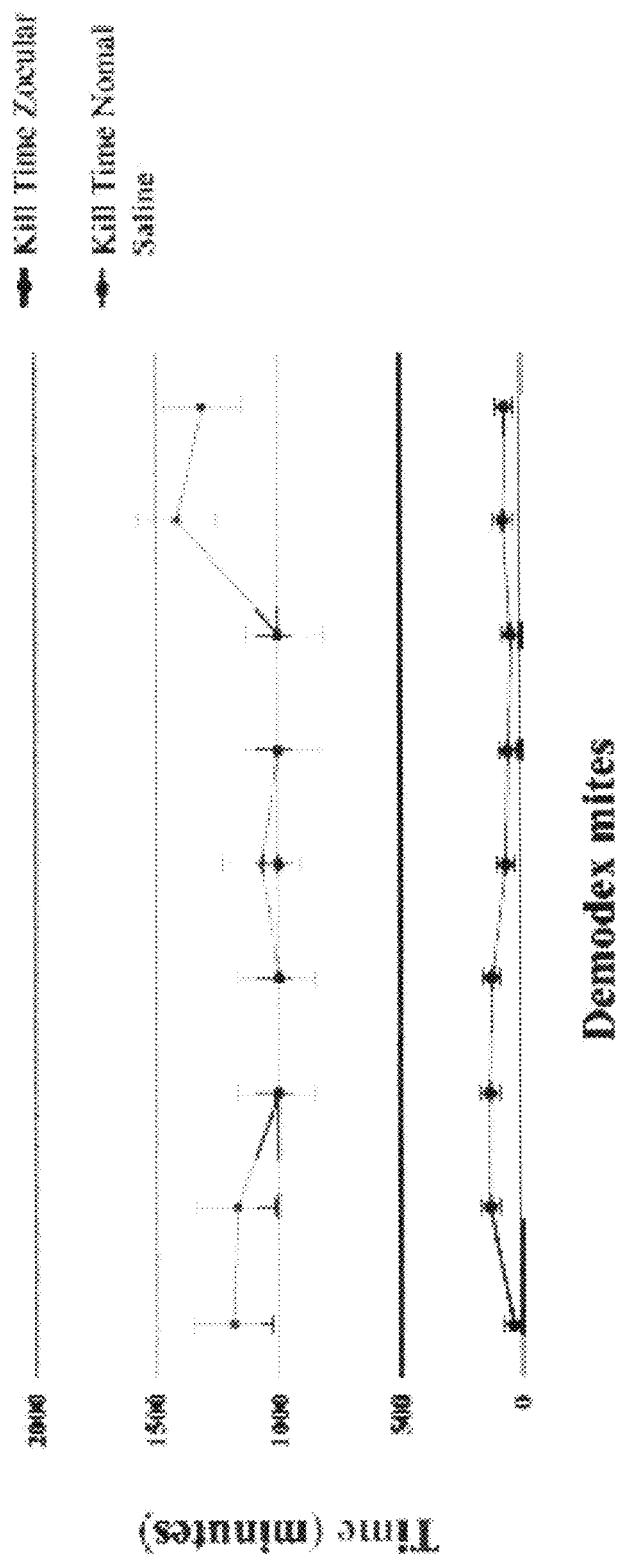
FIG. 5 illustrates the kill time of the formulation (Zocular) and normal saline.

The ZocuFoam™ scrub is especially helpful for patients who experience allergic reactions to various components of the TTO solution, such as *Eucalyptus*. This regimen is effective in killing and reducing *Demodex* presence. FIG. 5.

EXAMPLE 7

Figure 6:
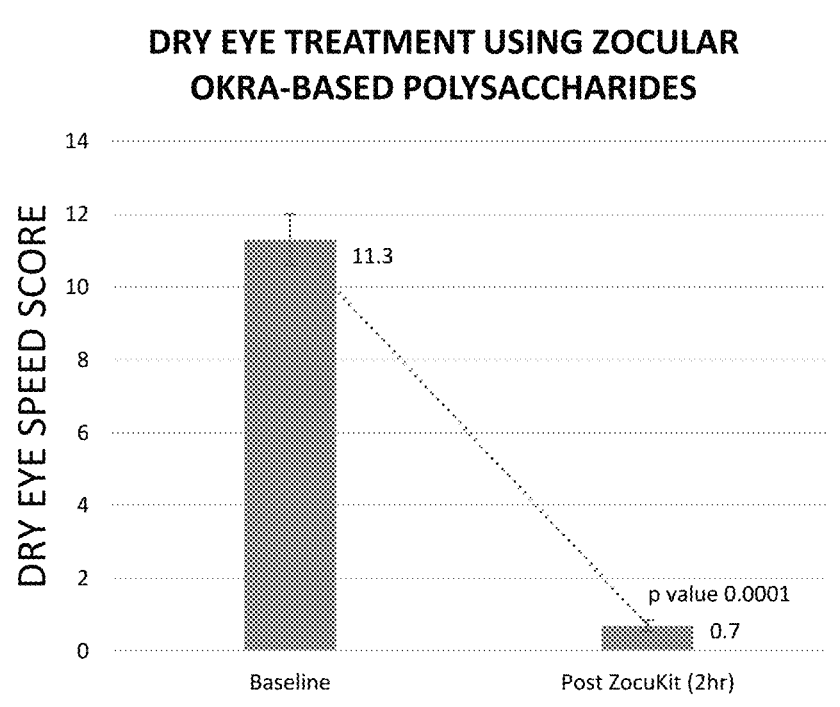
FIG. 6 depicts the results of dry eye treatment using Zocular okra-based polysaccharides. The graph shows the results of the Standard Patient Evaluation of Eye Dryness (SPEED) questionnaire at baseline before treatment and 2 hours after treatment with the ZocuKit (for ZEST treatment), a disposable kit that contains lid cleaning accessories and a gel with okra-based polysaccharides.

An in-office eyelid debridement using a okra-based polysaccharide gel was performed to evaluate the gel for dry eye relief. Evaluation was performed using a SPEED questionnaire. Subjects with a SPEED Score over 6 and who were 18 years or older were eligible for this study. Exclusion criteria included smoking, pregnancy, active ocular infection or intraocular inflammation, recent eye surgery within the previous 3 months, or prior isotretinoin use. SPEED scores were taken at baseline and at 2 hours following bilateral eyelid debridement using the ZocuKit™ System containing the okra-based polysaccharide gel. At baseline, the mean SPEED score was 11.3±0.7 in 9 subjects. FIG. 6. Two hours after eyelid debridement with an okra-based polysaccharide gel, the mean SPEED score improved to 0.7±0.3 (p<0.0001). FIG. 6. The results demonstrate an improvement in all treated subjects with moderate to severe dry eye symptoms using an okra-based polysaccharide gel for controlling inflammation at the eyelid margin. Schachter. The SPEED questionnaire assesses pain via the score for soreness and burning.

EXAMPLE 8

Figure 7A:
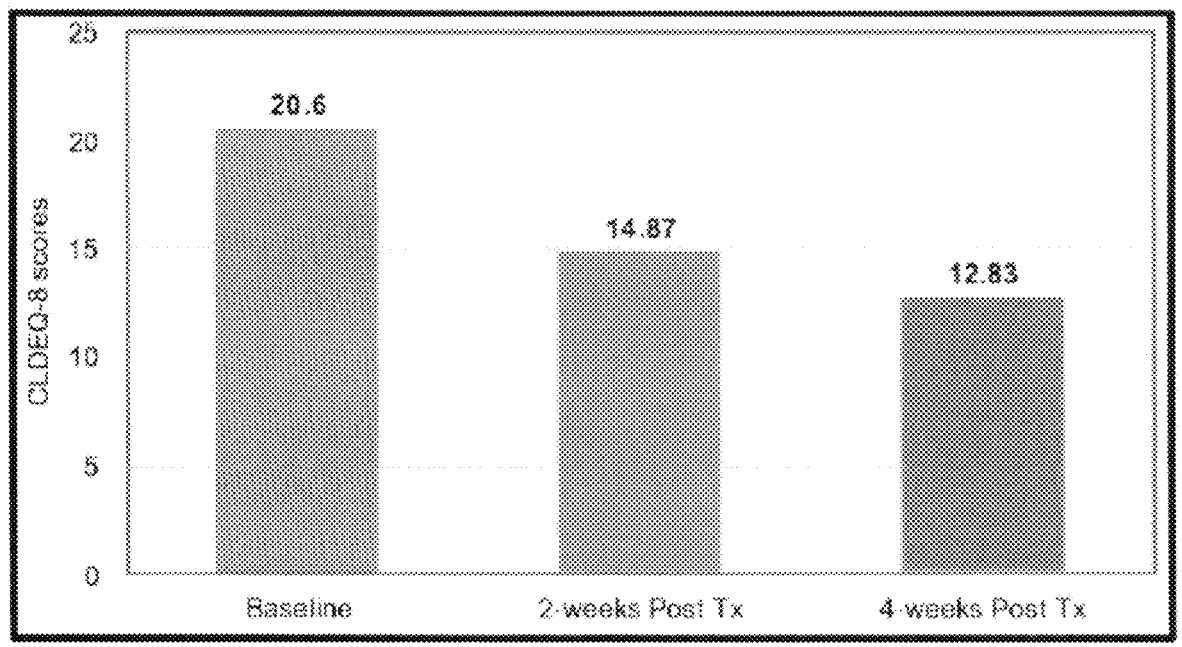
FIG. 7A depicts dry eye symptoms associated with contact lens use as measured with the Contact Lens Dry Eye Questionnaire-8 (CLDEQ-8), which shows improved (lower) scores after Zocular Eyelid System Treatment (ZEST) treatment.
Figure 7B:
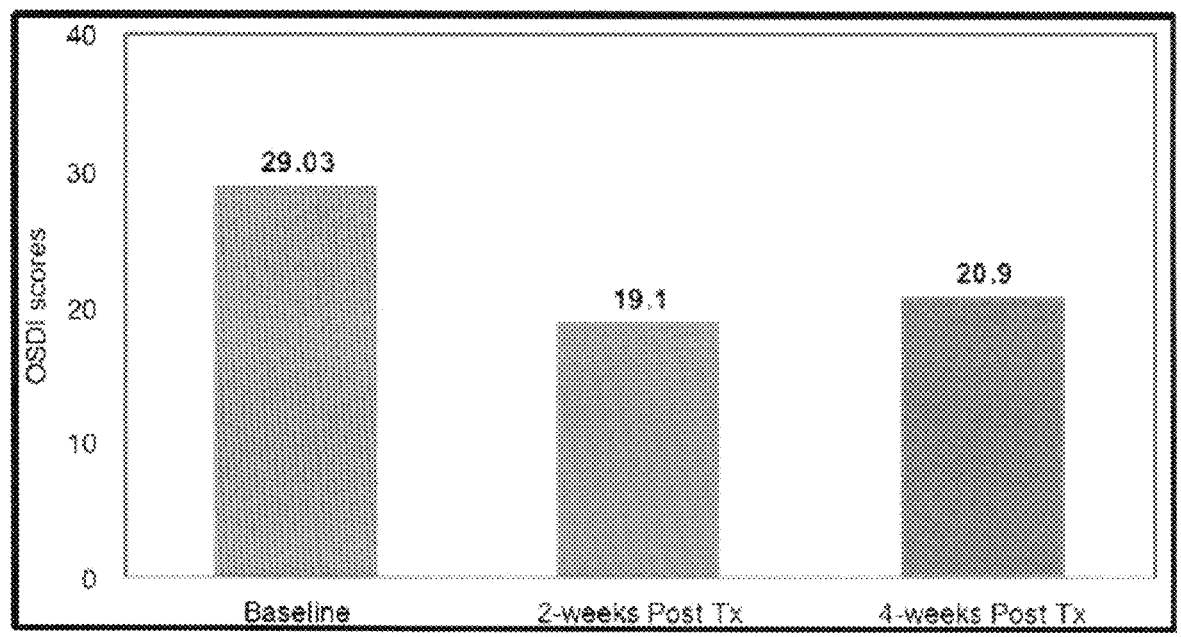
FIG. 7B depicts improved (lower) Ocular Surface Disease Index (OSDI) scores after ZEST treatment.
Figure 7C:
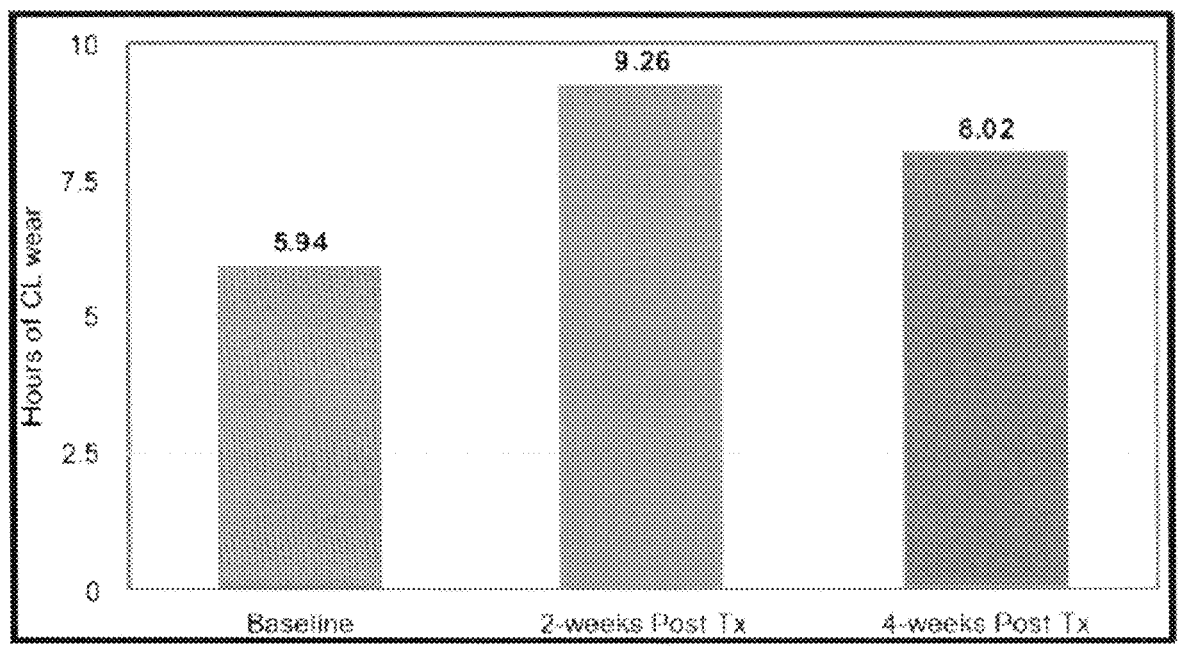
FIG. 7C depicts increased contact lens (CL) wear time after ZEST treatment.
Figure 7D:
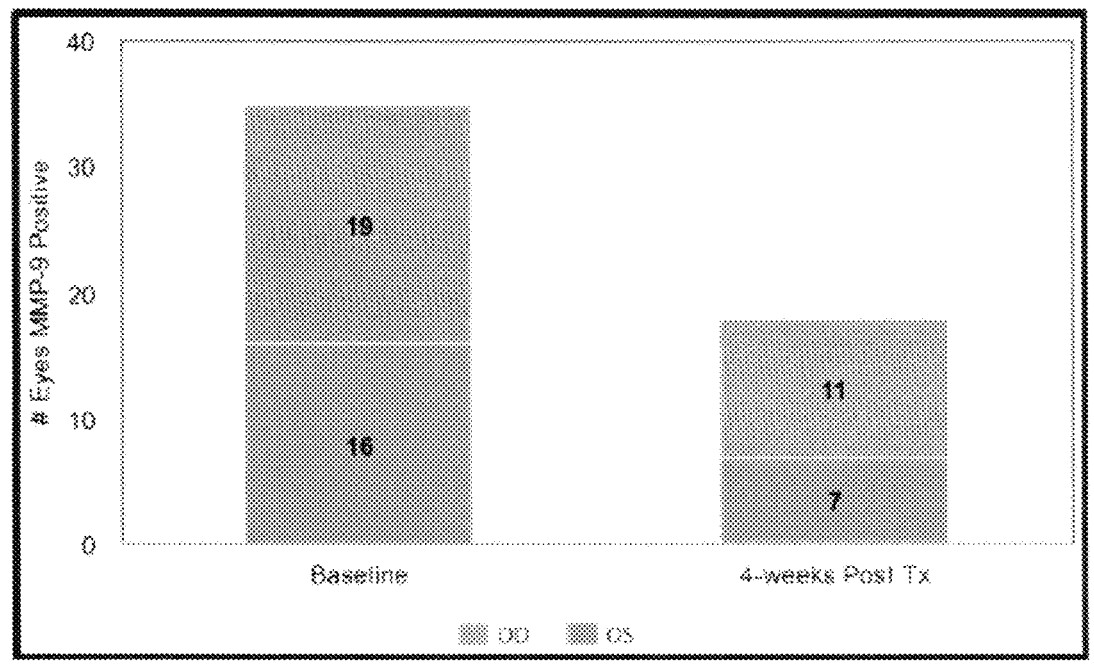
FIG. 7D depicts the disappearance of the inflammatory marker Matrix Metallopeptidase-9 (MMP-9) after ZEST treatment for the right eye (oculus dexter (OD)) and left eye (oculus sinister (OS)).

The purpose of these tests were to evaluate contact lens discomfort (CLD) associated with meibomian gland disfunction (MGD) using the Zocular Eyelid System Treatment (ZEST) protocol. ZEST was performed in all eyelids on thirty CLD patients with MGD (26.5+/−7.51 years) on the first visit. Patients reported the number of hours of contact lens (CL) wear per day (FIG. 7C) and completed the CLDEQ-8 questionnaire (FIG. 7A) prior to treatment and at 2-weeks and 1-month post treatment. A Quidel® Inflammadry® MMP-9 test was done prior to and 1-month post-treatment. FIG. 7D. Non-invasive tear break-up (NITBUT) was measured at each visit. Ocular Surface Disease Index (OSDI) scores were measured prior to treatment and at 2-weeks and 1-month post treatment. FIG. 7B. Data was analyzed by paired samples t-test. Narayanan et al. The OSDI questionnaire assesses pain via a sore eyes question.

Any patents or publications mentioned in this specification are indicative of the levels of those skilled in the art to which the disclosure pertains. These patents and publications are herein incorporated by reference to the same extent as if each individual publication was specifically and individually indicated to be incorporated by reference.

Changes therein and other uses will occur to those skilled in the art which are encompassed within the spirit of the disclosure as defined by the scope of the claims.

REFERENCES

The following references were cited herein:
U.S. Pat. No. 4,014,335, Arnold, Randall K., Ocular Drug Delivery Device, Mar. 29, 1977.
U.S. Pat. No. 4,154,822, Polimeni et al., Polysaccharide for Enhancement of Cardiac Output, May 15, 1979.
U.S. Pat. No. 5,851,963, O'Bryant, Jeffrey Charles. Organic Lubricant, Dec. 22, 1998.
U.S. Pat. No. 6,124,248, O'Bryant, et al., Organic Lubricants and Coolants, Sep. 26, 2000.
U.S. Pat. No. 8,628,816, Henry et al., Product to reduce glycemic response of carbohydrate based foods, Jan. 14, 2014.
U.S. Pat. No. 9,163,374, Alcantar, et al., Use of cactus mucilage as a dispersant and absorbent for oil in oil-water mixtures, Oct. 15, 2015.
US Patent Application No. 20140303094, Bastia et al., Composition and Use Thereof in the Treatment of Anal Rhagades, Oct. 9, 2014.
Sindhu, G.; Ratheesh, M.; Shyni, G. L.; Nambisan, B.; and Helen, A., Anti-inflammatory and antioxidative effects of mucilage of *Trigonella foenum graecum* (Fenugreek) on adjuvant induced arthritic rats, Intl. Immunopharm. 12: 205-211 (2012).
Cosmetic Ingredients Database, available at http://www.r-sc.org/education/teachers/Resources/aflchem/resources/39/39%20resources/39-2%20database.pdf.
Farooq, U.; Malviya, R.; and Sharma, P. K., Extraction and Characterization of Okra Mucilage as Pharmaceutical Excipient, Acad. J. Plant. Sci. 6(4):168-172 (2013).
Gao Y Y, Di Pascuale M, Li W, et al., In vitro and in vivo killing of ocular *Demodex* by tea tree oil. British Journal of Ophthalmology 2005, 89: p. 1468-1473.
Gao Y Y, Di Pascuale M, Li W, et al., High Prevalence of *Demodex* in eyelashes with cylindrical Dandruff. Investigative Ophthalmology & Visual Science. 2005, 46(9): p. 3089-94.
Inceboz T, Yaman A, Over Leyla, et al., Diagnosis and Treatment of Demodetic Blepharitis. Turkiye Parazitoloji Dergisi. 2009, 33(1): p. 32-36.
Narayan S, Bendert E, Owen K, Zamaron T, Lopez C, and Kasraie N, ZEST—Zocular Eyelid System Treatment—improves contact lens discomfort caused by MGD, Poster at Optometry's Meeting.
Schachter S, Novel Okra Polysaccharide Approach to Inflammation Control for Dry Eye, ARVO Study.
Liu and Gong, Experimental and Therapeutic Medicine, 2021, 21: p. 338-345.

What is claimed is:

1. A formulation for treating inflammation in a bodily tissue comprising:
   a mucilage extracted from *Abelmoschus*, wherein said mucilage is present in the formulation at a concentration of 0.001%-5.0% (w/v);
   one or more emollients, wherein said emollients are selected from the group consisting of *Aloe barbadensis* leaf juice and glycerin; and
   one or more antioxidants, wherein said antioxidants are selected from the group consisting of *Rubus idaeus* seed oil and *Citrus unshiu* peel extract;
   wherein said formulation is intended to be applied to a bodily tissue selected from the group comprising external tissues and mucosal tissues, and said formulation treats inflammation in said bodily tissue.

2. The formulation of claim 1, wherein the mucilage is extracted from *Abelmoschus esculentus*.

3. The formulation of claim 2, wherein the mucilage is extracted from plant material selected from the group consisting of fresh plant material, frozen plant material, dried plant material, and powdered plant material.

4. The formulation of claim 3, wherein the *Abelmoschus esculentus* mucilage is extracted from powdered okra.

5. The formulation of claim 1, further comprising one or more surfactants.

6. The formulation of claim 5, wherein the one or more surfactants are selected from the group consisting of disodium laureth sulfosuccinate, decyl glucoside, cetalkonium chloride, disodium cocoamphodiacetate, and glycerin.

7. The formulation of claim 1, further comprising caffeine as an antioxidant; sodium phytate as a chelating agent; hydrolyzed soy protein as a moisturizer; ethylhexylglycerin as a conditioning agent and preservative; and phenoxyethanol as a preservative.

8. The formulation of claim 1, wherein the formulation is provided in a form selected from the group consisting of a wipe; a swab; a bandage; a gauze; a suspension; a foam; a gel; and a spray.

9. The formulation of claim 8 wherein the formulation is a gel.

10. The formulation of claim 1, wherein the formulation is buffered to a pH range of about 5.5 to 8.0.

11. The formulation of claim 10, wherein the formulation is buffered to a pH of about 6.5.

12. The formulation of claim 10, wherein the formulation is buffered with one of more salts selected from the list consisting of sodium chloride, sodium lactate, potassium chloride, and calcium chloride.

13. The formulation of claim 12, wherein the formulation further comprises one or more cationic, anionic, nonionic, or amphoteric surfactants.

14. A formulation for treating pain in a bodily tissue comprising:
   a mucilage extracted from *Abelmoschus*, wherein said mucilage is present in the formulation at a concentration of 0.001%-5.0% (w/v);
   one or more emollients, wherein said emollients are selected from the group consisting of *Aloe barbadensis* leaf juice and glycerin; and
   one or more antioxidants, wherein said antioxidants are selected from the group consisting of *Rubus idaeus* seed oil and *Citrus unshiu* peel extract;
   wherein said formulation is intended to be applied to a bodily tissue selected from the group comprising external tissues and mucosal tissues, and said formulation treats pain in said bodily tissue.

15. The formulation of claim 14 wherein the formulation is an anti-pain formulation comprising *Abelmoschus esculentus* mucilage; *Rubus idaeus* seed oil; *Citrus unshiu* peel extract; *Aloe barbadensis* leaf juice; sodium phytate; phenoxyethanol; and ethylhexylglycerin; and wherein the formulation is buffered to a pH range of about 5.5 to 8.0.

16. The formulation of claim 14 wherein the formulation is a gel.

17. The formulation of claim 14, wherein the formulation is provided in a form selected from the group consisting of a wipe; a swab; a bandage; a gauze; a suspension; a foam; a gel; and a spray.

18. A method of treating inflammation in a bodily tissue comprising:
   preparing the formulation of claim 1; and
   applying the formulation to the bodily tissue in need of inflammation treatment.

19. A method of treating pain in a bodily tissue comprising:
    preparing the formulation of claim 14; and
    applying the formulation to the bodily tissue in need of pain treatment.

20. A method of treating pain in a bodily tissue or an inflamed bodily tissue comprising:
    applying to the bodily tissue in need of pain treatment or the inflamed bodily tissue a formulation comprising *Abelmoschus esculentus* mucilage; *Rubus idaeus* seed oil; *Citrus unshiu* peel extract; *Aloe barbadensis* leaf juice; disodium laureth sulfosuccinate; decyl glucoside; disodium cocoamphodiacetate; glycerin; caffeine; sodium phytate; hydrolyzed soy protein; phenoxyethanol; ethylhexylglycerin; sodium chloride; sodium lactate, potassium chloride, and calcium chloride; and wherein the formulation is buffered to about pH 6.5.

21. The method of claim 20 wherein the formulation is absorbed through the skin or mucosal membrane.

* * * * *